United States Patent
Ho et al.

(10) Patent No.: US 7,407,817 B2
(45) Date of Patent: Aug. 5, 2008

(54) SURFACE PLASMON RESONANCE SENSORS AND METHOD FOR DETECTING SAMPLES USING THE SAME

(75) Inventors: Ho Pui Ho, Hong Kong (CN); Shu Yuen Wu, Hong Kong (CN); Chinlon Lin, Hong Kong (CN); Siu Kai Kong, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 385 days.

(21) Appl. No.: 11/337,034

(22) Filed: Jan. 19, 2006

(65) Prior Publication Data

US 2007/0166763 A1   Jul. 19, 2007

(51) Int. Cl.
G01N 33/551 (2006.01)
G01N 33/553 (2006.01)

(52) U.S. Cl. .................. 436/524; 349/56; 356/317; 356/323; 356/364; 356/369; 356/491; 359/237; 359/246; 385/12; 385/129; 385/130; 422/82.11; 435/287.2; 435/288.7; 435/808; 436/164; 436/518; 436/525; 436/805

(58) Field of Classification Search ............... None
See application file for complete search history.

(56) References Cited

U.S. PATENT DOCUMENTS 5,627,666 A   5/1997   Sharp et al.

2002/0180979 A1   12/2002   Chou et al.
2003/0030817 A1*   2/2003   Lee et al. ............... 356/491
2003/0103208 A1   6/2003   Quinn et al.

FOREIGN PATENT DOCUMENTS

| CN | 1237705 | 12/1999 |
| CN | 1342894 | 4/2002 |
| CN | 1393689 | 1/2003 |
| CN | 1588064 | 3/2005 |

OTHER PUBLICATIONS

A.V. Kabashin, et al, Surface plasmon resonance interferometer for bio- and chemical-sensors, Optics Communications 150, p. 5-8, May 1, 1998.

(Continued)

*Primary Examiner*—Christopher L Chin
(74) *Attorney, Agent, or Firm*—Darby & Darby PC; Bruce E. Black

(57) ABSTRACT

Disclosed is an optical sensing device including a source unit providing a beam of light with continuously modulated phase retardation between p- and s-polarization components of the light by employing a LCM; a reference unit receiving a first part of the light to provide a reference signal; a SPR sensing unit receiving a second part of the light to induce a phase retardation change between the p- and s-polarization components due to SPR associated with a sample; a probe unit receiving the light after SPR to provide a probe signal; and a detection unit connected to the reference unit and the probe unit to detect characteristics of the sample by comparing the reference signal with the probe signal. By using active phase modulation technologies and differential phase measurement, it is possible to fulfill chemical and biological detection.

25 Claims, 12 Drawing Sheets

OTHER PUBLICATIONS

J. Homola et al., Surface plasmon resonance sensors: review, Sensors and Actuators B 54, 1999, p. 3-15.

H. P. Ho, et al, Surface plasmon resonance sensor based on the measurement of different phase, Review of Scientific Instruments, vol. 73, No. 10, Oct. 2002, p. 3534-3539.

P. I. Nikitin, et al, Surface plasmon resonance interferometry for micro-array biosensing, Sensors and Actuators 85, 2000, p. 189-193.

S. G. Nelson, et al, High sensitivity surface plasmon resonance sensor based on phase detection, Sensors and Actuators B 35-36, 1996, p. 187-191.

Shuai Shen, et al, Optical phase-shift detection of surface plasmon resonance, Applied Optics, vol. 37, No. 10, Apr. 1, 1998, p. 1747-1751.

Radan Slavik, et al, Miniaturization of fiber optic surface plasmon resonance sensor, Sensors and Actuators B 51, 1998, p. 311-315.

\* cited by examiner

SURFACE PLASMON RESONANCE SENSORS AND METHOD FOR DETECTING SAMPLES USING THE SAME

TECHNICAL FIELD OF THE INVENTION

This invention relates to an optical sensing device for chemical and biological detection, and more particularly to a surface plasmon resonance (SPR) sensor which provides a simple and accurate SPR phase measurement by making use of a birefringence of a liquid crystal modulator (LCM) to continuously modulate a phase difference between s-polarization and p-polarization.

BACKGROUND OF THE INVENTION

SPR sensors have been widely used in a variety of disciplines such as chemical, biochemical, biological, biomedical analysis, pollution monitoring, and process control.

SPR is the result of optical excitation of a surface plasmon wave (SPW) along an interface between a conducting material and a non-conducting material. A common technique for their creation is to direct a beam of electromagnetic radiation into a glass prism with an angle of incidence above the critical angle so that it undergoes total internal reflection. The internal reflection creates an evanescent electromagnetic wave at a region outside of the prism adjacent to the surface. When a thin conductive film such as gold or silver is deposited on the surface of the prism, surface plasmons will be formed.

Various types of optical sensors relying upon SPR measurement have been reported. These sensing techniques are primarily concerned with analyzing the angle, wavelength or phase properties of the reflected beam to extract the SPR information (Sensors and Actuators B, 54, 3-15, 1999). There are two most popular sensing schemes. One is the angular interrogation scheme which involves a monochromatic light source and measuring the intensity variation of the reflected beam at a range. The other is the wavelength interrogation scheme which uses a broadband light source and obtains SPR information by observing the spectral intensity variation at a fixed illumination angle.

In fact, SPR affects not only the intensity of the reflected light beam but also its optical phase at the same time. Researchers including us have found that the phase response has a steep slope near the SPR absorption dip (Optical Communication, 150, 5-8, 1998). Based on this property, phase interrogation has been estimated to provide extremely high sensing accuracy.

The first practical SPR phase measurement system was based on heterodyne interferometry (Sensors and Actuators B, 35-36, 187-191, 1996). It used an acousto-optical modulator (AOM) to modulate the signal in high frequency at 140 MHz. In order to obtain the phase information, a local oscillator was employed to shift the AOM modulation frequency at 10 kHz so that a phase meter may be employed to measure the phase difference between the reference and the probe signals. The paper describes that the estimated sensitivity, because of SPR phase measurement, has three times improvement compared to the conventional scheme. Although this sensing scheme can extract the SPR phase information from the reflected beam, the design is rather complicated both in the optical and electronic sections. In the optical part, it requires very precise optical alignment when the two optical beams are recombined again to ensure formation of detectable interference fringes. In the electronics, there are also many high frequency mixes for processing the signal. In addition, the need of acousto-optical modulator (AOM) also inerrably increases system complexity as well as costs.

Later Guo et. al. (Applied Optics, 37, 1747-1751, 1998) demonstrated a much simplified heterodyne phase sensing system using a frequency-stabilized Zeeman laser. In their system the self-frequency shift between the s- and p-polarizations due to the Zeeman's effect is employed so that the s- and p-polarizations may interfere with each other. Thus, a beat signal, which appears at the photodetector, provides the phase quantity associated with the SPR effect. The beat frequency signal ranges between tens of kilohertz to several mega-hertz. Such a high frequency is too fast to image analysis except using expensive high-speed CCD cameras. Therefore, this technique may only find applications in single sensor instruments.

More recently, a static Mach-Zehnder interferometer has been used by Nikitin et. al. (Sensors and Actuators B, 85, 189-193, 2000), for performing two-dimension SPR phase imaging. The main drawback of this design is that the system is very sensitive to mechanical movements in the optical components. Small mechanical vibrations in the mirrors or variations of temperature will inevitably cause the optical beam to move and thus leading to phase measurement error (Review of Scientific instruments, 73, 3534-3539, 2002).

It has been reported that ellipsometric measurement (Sensors and Actuators B, 51, 331-339, 1998) can also provide SPR phase information. But the drawback is that this technique involves rather cumbersome procedures. Ellipsometry equipments, whether using white light or a laser beam, are very slow machines in which several mechanical components including the polarization analyzer, the wavelength spectrometer and the goniometers are required to change position mechanically in order to obtain information. For SPR applications, which usually require real-time signal reporting, the slow speed from commercial ellipsometers is a major disadvantage.

SUMMARY OF THE INVENTION

It is an object of the invention to provide a simple device which can perform accurate SPR phase measurement on a two-dimensional level so as to analyze biological, biochemical, or chemical characteristics of a sample.

To achieve the above object, the present invention discloses a method and a SPR sensing device for chemical and biological detection by employing an active phase modulation through a liquid crystal modulator (LCM) and a differential phase measurement technique.

According to an aspect of the present invention, an optical sensing device comprises a source unit which includes a source emitting a beam of light containing p- and s-polarization components and a phase modulator modulating a phase retardation between the p- and s-polarization components; a reference unit for receiving and detecting a first part of the light to provide a reference signal indicating the modulated phase retardation; a SPR sensing unit for receiving a second part of the light to induce a phase retardation change between the p- and s-polarization components due to SPR associated with a sample; a probe unit for receiving the light passing the SPR sensing unit to provide a probe signal indicating the phase retardation change induced by the SPR sensing unit; and a detection unit, coupled between the reference unit and the probe unit to detect biological, biochemical, or chemical characteristics of the sample by comparing the reference signal with the probe signal.

According to an embodiment of the present invention, the phase modulator may be an LCM. The orientation of the liquid crystal can be controlled by a drive voltage of the LCM, so that the phase retardation between the p- and s-polarization components can be continuously modulated by varying the drive voltage of LCM.

According to another embodiment of the present invention, the source unit may further comprise a polarizer for setting an intensity ratio between the p- and s-polarization components of the light emitted from the source to achieve a high signal-to-noise ratio.

According to another aspect of the present invention, a method for detecting biological, biochemical, or chemical characteristics of a sample comprises: transmitting a beam of light containing p-polarization and s-polarization components; modulating a phase retardation between the p-polarization and s-polarization components; providing a reference signal indicating the phase retardation by receiving a first part of the light; receiving a second part of the light to induce a phase retardation change between the p-polarization and s-polarization components due to SPR associated with a sample; providing a probe signal indicating the phase retardation change by receiving the light after SPR associated with the sample; and detecting biological, biochemical, or chemical characteristics of the sample by comparing the probe signal with the reference signal.

As stated above, the reference unit is used for providing information on phase retardation introduced by LCM, while the probe unit provides the information of phase retardation change due to SPR in addition to that induced by LCM. Direct subtraction between the phase values obtained from the probe unit and the reference unit leads to the measurement of SPR phase change. The LCM plays an important role in the invention, because it can continuously modulate the phase retardation, which enables self-interference between the s- and p-polarization so that signals (e.g., images) captured before and after the beam passing the SPR sensor may be transformed into SPR differential phase signals. Therefore, it is possible to perform accurate SPR phase measurement on a two-dimensional level so that any local variations of phase retardation change due to the SPR sensor may be detected. We now have a single beam interferometer (i.e. no need of a separate reference beam) with inherent noise immunity. The optical setup becomes extremely simple.

The key features of this invention are: i) using a differential phase measurement technique to improve sensing accuracy by eliminating all common-mode phase noise, that is, the measurement only corresponding to the phase change induced by the SPR effect; ii) using an active phase modulation technique through an LCM to actively modulate the light beam which thereby greatly reduces system hardware complexity.

The SPR sensor of the present invention provides many advantages. First it offers higher sensitivity measurement in refractive index changes near on the sensing surface. Second, the stability of phase measurement is enhanced by using differential phase measurement technique, which reduces disturbance from the environment. Third, the invention can be used in a range of different applications where real time SPR phase imaging measurement is needed. Fourth, the system design is simple and low cost both in its optical and electronic parts. Fifth, the invention may be easily adapted for use in different types of SPR coupling schemes. Sixth, its small size and low power consumption make it well suited for compact and portable system.

DETAILED DESCRIPTION OF THE INVENTION

The present invention and various advantages thereof will be described with reference to exemplary embodiments in conjunction with the drawings.

Figure 1:
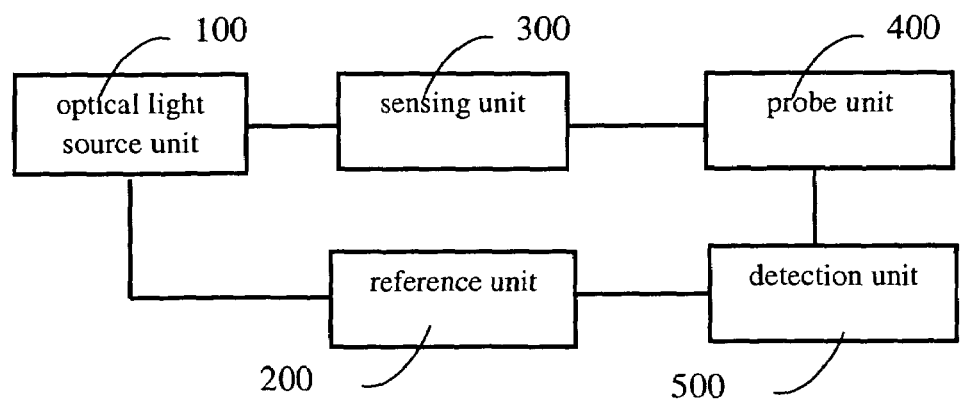
FIG. 1 is a block diagram of a SPR sensor according to the present invention.

FIG. 1 illustrates an embodiment of a phase SPR sensor in accordance with the present invention. In the embodiment, the phase SPR sensor comprises: an optical light source unit 100 for providing a beam of light containing p- and s-polarization components with a modulated phase retardation between the p- and s-polarization components; a reference unit 200 for receiving one portion of the beam to provide a reference signal indicating the modulated phase retardation; a sensing unit 300 for receiving another portion of the beam to induce a phase retardation change between the p- and s-polarization components due to SPR associated with a sample; a probe unit 400 for receiving the light passing the SPR sensing unit so as to provide a probe signal indicating the phase retardation change induced by the SPR sensing unit; and a detection unit 500 connected to the reference unit and the probe unit to detect characteristics of the sample by comparing the reference signal with the probe signal.

Figure 2:
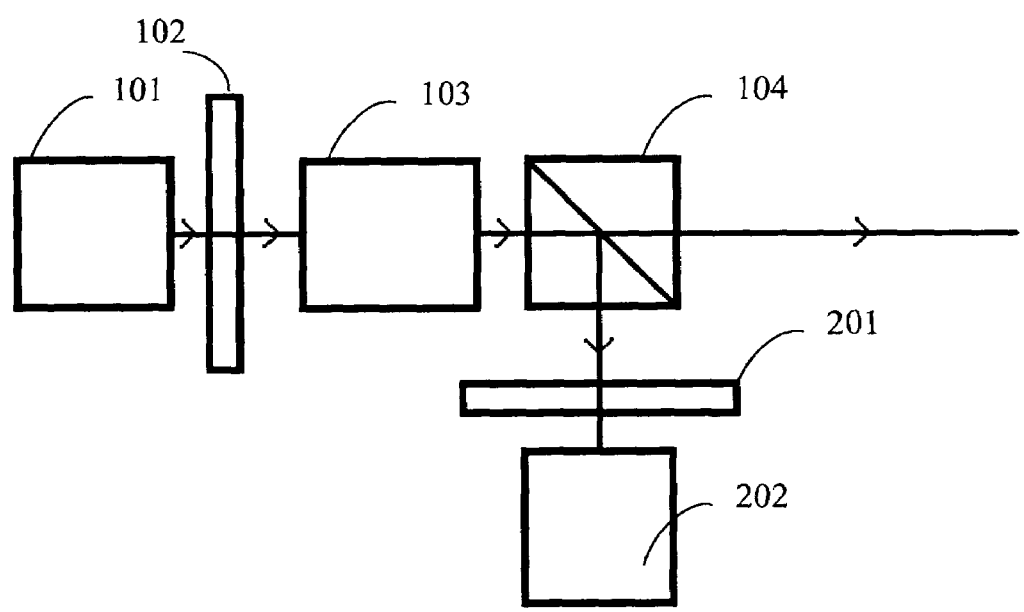
FIG. 2 is a schematic view of an optical light source unit and a reference unit illustrated in FIG. 1.

As shown in FIG. 2, the optical light source unit 100 comprises an electromagnetic radiation source 101, a polarizer 102, a phase modulator 103, and a beam splitter 104.

The electromagnetic radiation source 101 may comprise a gas laser, a solid state laser, a laser diode, a light emitting diode (LED), a broad band white light source or any other suitable electromagnetic radiation source. Preferably, a linear polarization He—Ne laser with optical output power of 12 mW is employed in the embodiment. The radiation source 101 is required to emit a beam of light containing s- and p-polarization components and the polarization of the output light beam is preferably set at 45° off the p-polarization.

The polarizer 102 is provided to select an intensity ratio between the p- and s-polarizations by turning a polarization angle of the polarizer 102. The polarization angle of the polarizer 102 is set at 45° off to p-polarization optical axis to obtain an equal intensity in both p- and s-polarizations.

Figure 3:
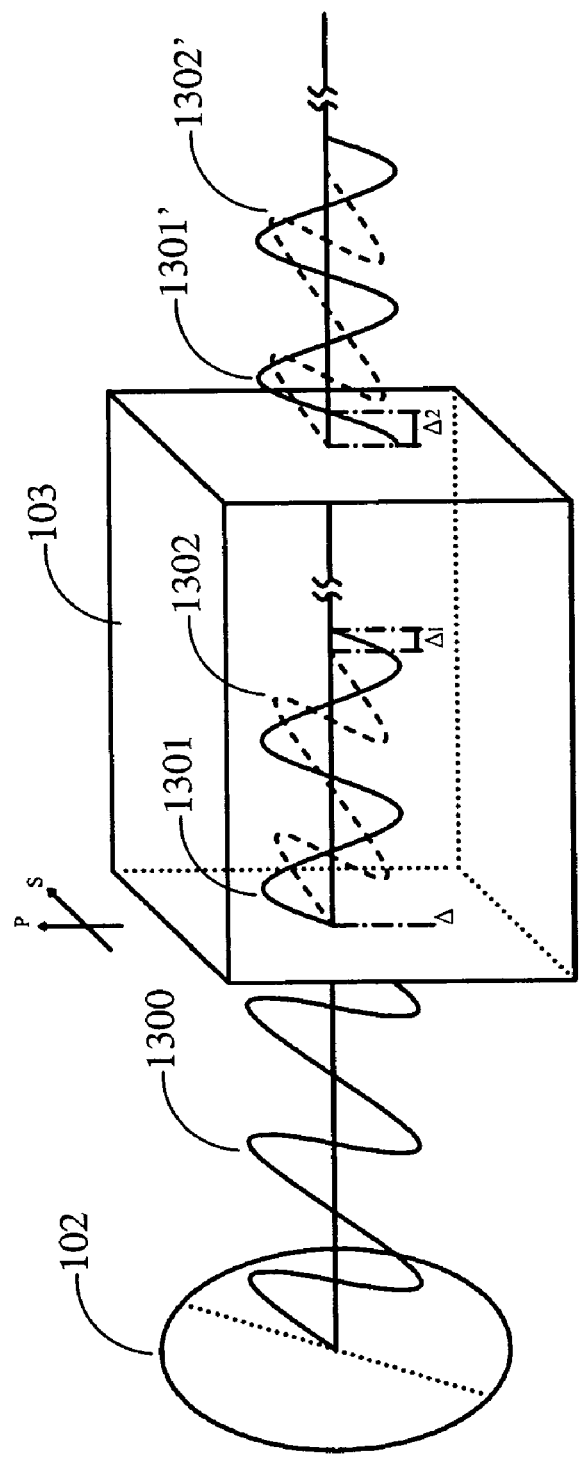
FIG. 3 is a schematic view showing principles of a liquid crystal modulator illustrated in FIG. 1.

The phase modulator 103 is a liquid crystal modulator (LCM) for modulating the optical phase retardation between the p- and s-polarization components. The fast axis of the LCM 103 may be matched with the optical axis of p- or s-polarizations to increase a modulation depth. The modulation principle is described as shown in FIG. 3. The LCM 103 receives a light 1300 passing through the polarizer 102. Propagation speeds of p-polarization component 1301 and s-polarization component 1302 of the light 1300 within the LCM 103 depend on the orientation of the liquid crystal inside the LCM 103. In here, the orientation of the liquid crystal can be controlled by a drive voltage of the LCM 103. That is, the propagation speeds of the p- and s-polarization components 1301 and 1302 can be controlled by the drive voltage. For example, at the beginning of the LCM 103, the phase retardation between the p- and s-polarization components 1301 and 1302 is $\Delta=0$. During the propagation of the p- and s-polarization components 1301 and 1302 within the LCM 103, the phase retardation therebetween is increased from $\Delta$ to $\Delta 1$. And, after passing through the LCM 103, a modulated phase retardation $\Delta 2$ is induced to the p- and s-polarization components 1301' and 1302'. Moreover, the modulated phase retardation $\Delta 2$ can be continuously changed by varying the drive voltage of LCM 103 in steps. According to the embodiment, the drive voltage of the LCM 103 is adjustable ranging from 0 to 13V and the frequency of the LCM 103 is set to be 10 Hz.

Figure 5:
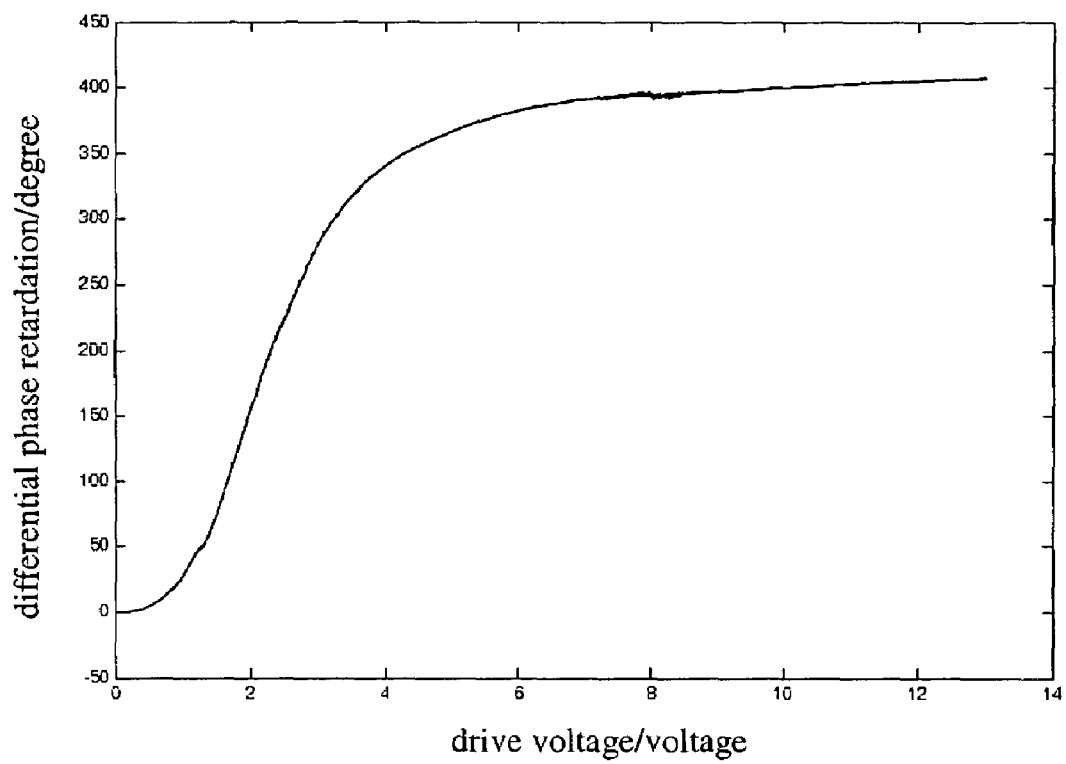
FIG. 5 shows the relationship between a phase retardation modulation and a drive voltage of a liquid crystal modulator.

A relationship between the phase retardation modulation and the drive voltage of the LCM 103 is measured and shown in FIG. 5. It is understood that the relationship of the phase retardation between p- and s-polarizations versus the input drive voltage is not a linear relationship. This non-linear characteristic may be easily converted back to a linear function via a pre-determined data transformation software program. Traditional SPR phase changes observed from the sample may be as high as $2\pi$. The embodiment is therefore required to perform phase retardation with the range from 0 to $2\pi$. Since a phase retardation of $\pi$ and $3\pi$ can generate identical interference fringe patterns, the only way to remove this ambiguity is to continuously keep track of the amount of the phase retardation being introduced to the light. Also, in order to precisely detect the phase retardation, the modulation depth of the phase retardation should be many cycles to $2\pi$. This is because final signal waveforms transformed using the pre-determined function will be a truncated sine wave, from which Fast Fourier Transform will produce required differential phase detection. One can improve detection precision if we increase the modulation depth, i.e., the number of cycles covered by the truncated since wave. We have proposed some solutions to resolve this problem in the following simple ways.

In order to achieve a sufficient modulation depth of the phase retardation, the LCM 103 can be configured as follows.

Figure 4A:
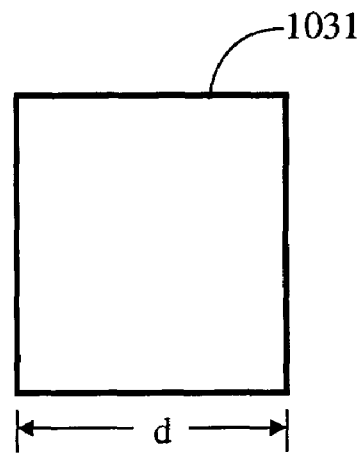
FIG. 4a shows a structure of an embodiment of a liquid crystal modulator of the liquid crystal modulator illustrated in FIG. 2.

As shown in FIG. 4a, a first embodiment of the LCM comprises one liquid crystal layer 1031. In this embodiment, a thickness, d, of the liquid crystal layer 1031 should be configured large enough to achieve a sufficient modulation depth of the phase retardation, which thereby requires a larger drive voltage and a further reduction in frequency response.

Figure 4B:
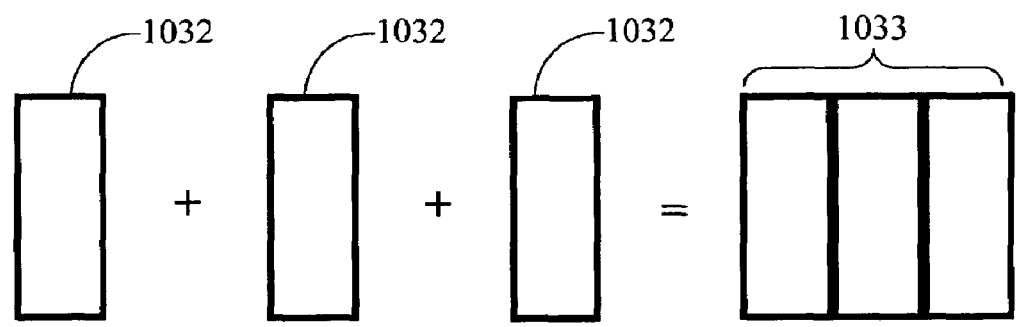
FIG. 4b shows a structure of another embodiment of a liquid crystal modulator of the liquid crystal modulator illustrated in FIG. 2.

As shown in FIG. 4b, a second embodiment of the LCM comprises two or more liquid crystal layers 1032 stacked together to form a multi-layered LCM 1033. This embodiment does not need a larger drive voltage, but requires several liquid crystal layers.

Figure 4C:
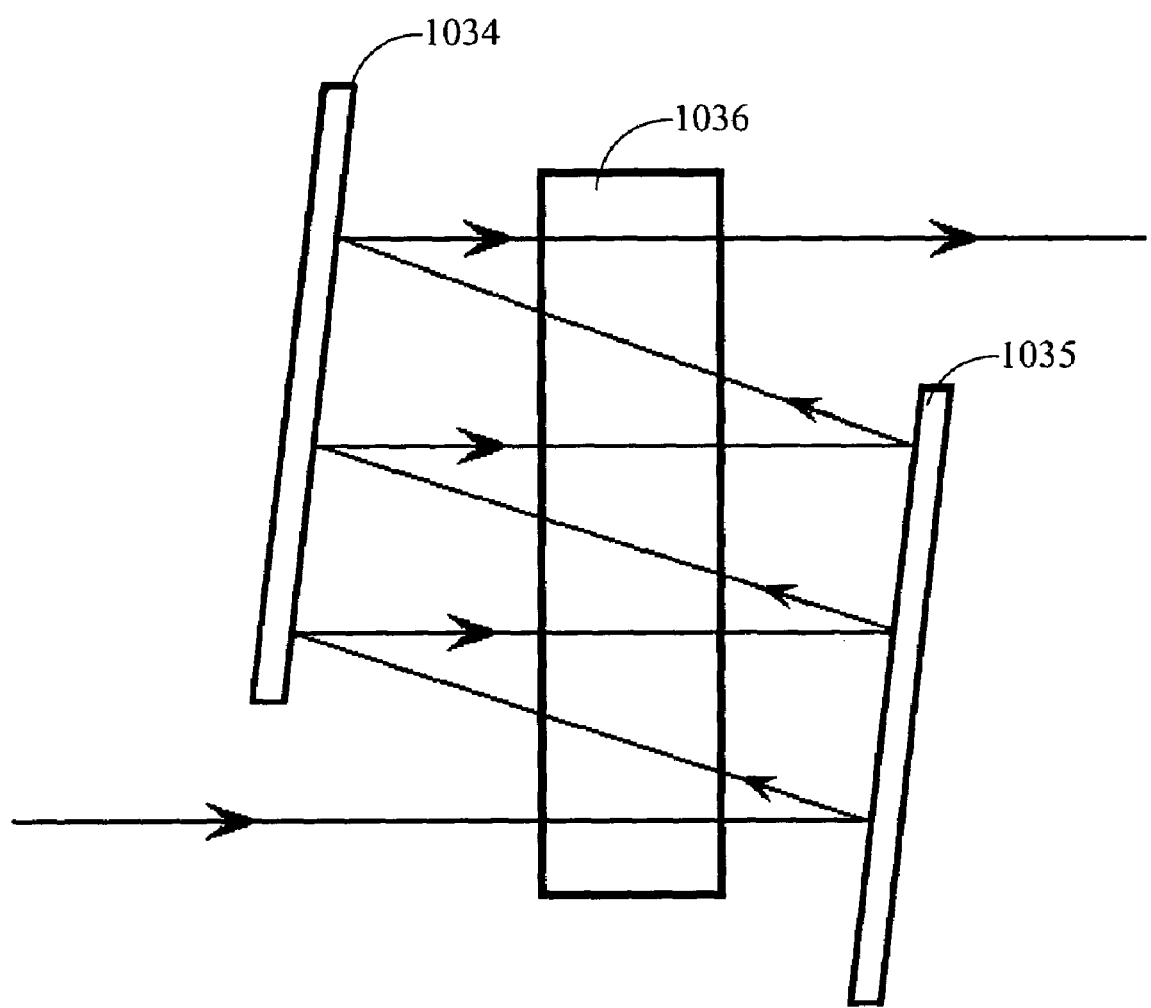
FIG. 4c shows a structure of a further embodiment of a liquid crystal modulator of the liquid crystal modulator illustrated in FIG. 2.

The configuration of a third embodiment of the LCM is described as shown in FIG. 4c. The LCM 1037 of this embodiment comprises a liquid crystal layer 1036 disposed between two mirrors 1034 and 1035. The position of the mirrors 1034 and 1035 is carefully configured so that the light can pass through the liquid crystal layer 1036 several times due to the reflection between the mirrors, which can thereby enhance the phase retardation. According to this embodiment, the modulation depth actually depends on the number of times that the optical beam passes through the liquid crystal layer 1036.

Figure 6A:
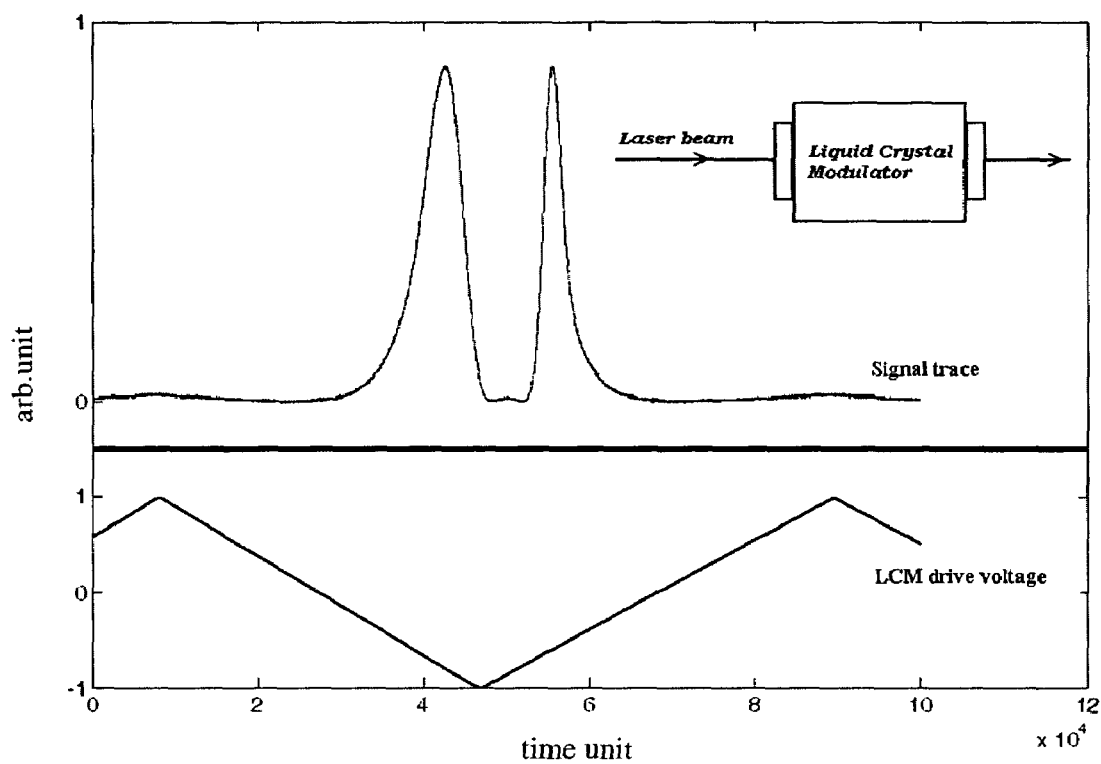
FIG. 6a and FIG. 6b show the modulation efficiencies of single pass and multi-pass enhance phase retardation methods.
Figure 6B:
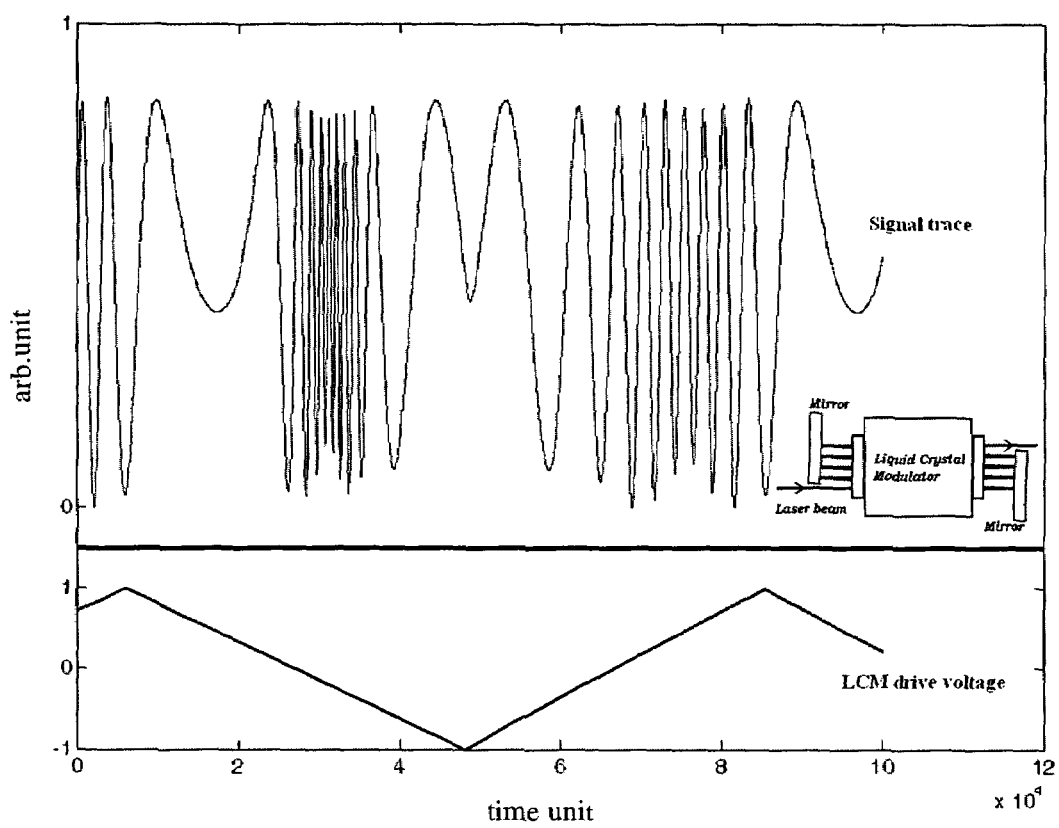

Measured signal traces according to both single pass and multi-pass methods are shown in FIG. 6a and FIG. 6b, respectively. It is understood from the figures, the multi-pass method has a high efficiency and a simple structure, which is demonstrated in the present invention. The triangular waveform shown in FIGS. 6a and 6b correspond to the drive voltage of the LCM 1031 and 1037, respectively. In the case of multi-pass modulation, since the beam-folding mirrors 1034 and 1035 will force the beam to go pass the liquid crystal layer 1036 a number of times, the aggregated modulation depth will increase accordingly in multiples of that of the single pass case. As seen from FIG. 6b, the signal trace goes through many more oscillations in each sweep cycle of the LCM drive voltage. The multi-pass method will ensure that the detected signal trace contains a higher level of spectral information, and consequently we can obtain a more accurate phase measurement from the signal trace. It is known that the retardation modulation provided by the LCM is not linearly proportional to the drive voltage. As a result the signal traces obtained from our setup in both cases are somewhat different from a pure sinusoidal waveform. However this non-linearity does not give any adverse effect on the final result when the differential phase measurement is conducted by first performing normalization of the two signal traces concerned. Then this is followed by performing point-wise signal amplitude subtraction along the horizontal time axis. The resultant signal tract will be a horizontal straight line with its position on the vertical amplitude axis proportional to the differential phase. The non-linearity introduced by the LCM will be automatically removed. Any small variations along this horizontal line will signify noise from phase jitters. The final differential phase value is obtained by taking an average of all the points along this horizontal line. The fact that we use the same procedures for all traces will ensure that no significant error will be introduced to the final differential phase value.

Now referring to FIG. 2, a beam splitter 104, which may be a blank glass slide, is used to separate the beam of light into two parts. One part is for a probe beam and the other, which is only 4% of input intensity, is for a reference beam. The reference beam can be obtained by the reference unit 200 which comprises a polarizer 201 and a photodetector 202. As shown in FIG. 2, the polarizer 201 is placed in front of the photodetector 202 for picking up the reference beam. The polarizer 201 is set at 45° relative to an optical axis of the p-polarization to generate an interference between the p- and s-polarization components. The photodetector 202 is used to detect the interference and convert an optical intensity variation of the interference to an electrical signal. Since the LCM 103 can permit phase retardation modulation of any format according to the present invention, it is possible to implement full-field SPR phase imaging simply by monitoring the SPR sensor surface in real-time using a photodetector 202 while the retardation phase is continuously increased in steps. According to the embodiment, the photodetector 202 can be a photo-diode or a photo charge coupled device (CCD). Apart from providing the required reference retardation phase, the output from the photodetector 202 also offers important information on the temperature characteristics of the LCM 103 which can later be used for providing a temperature compensation of the measured SPR phase.

Figure 7:
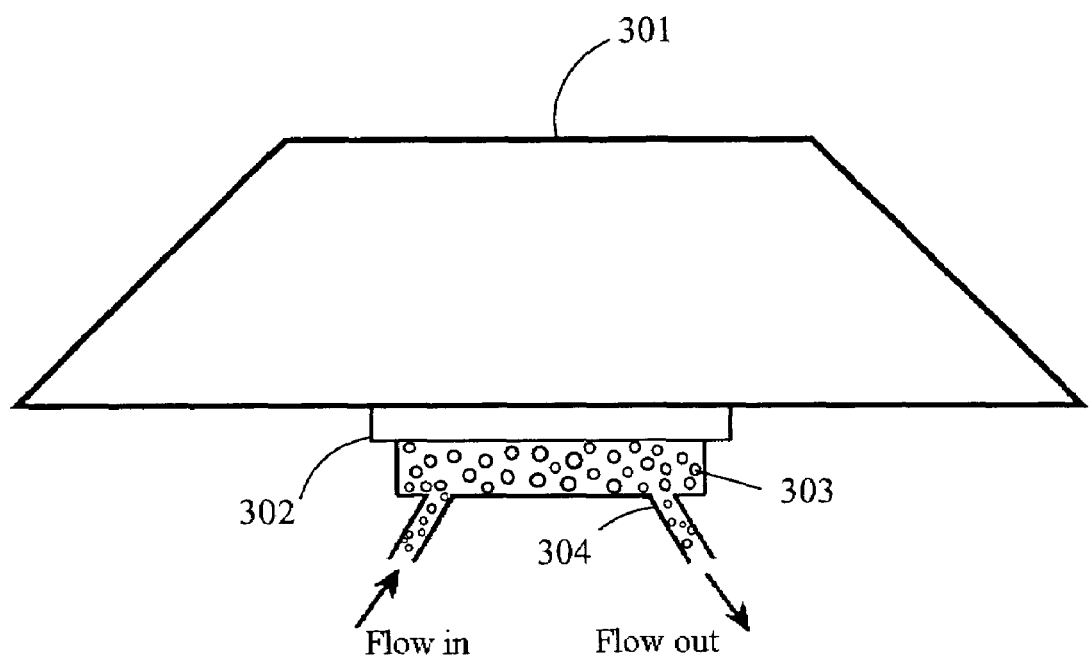
FIG. 7 shows the prism coupling scheme according to the present invention.
Figure 8:
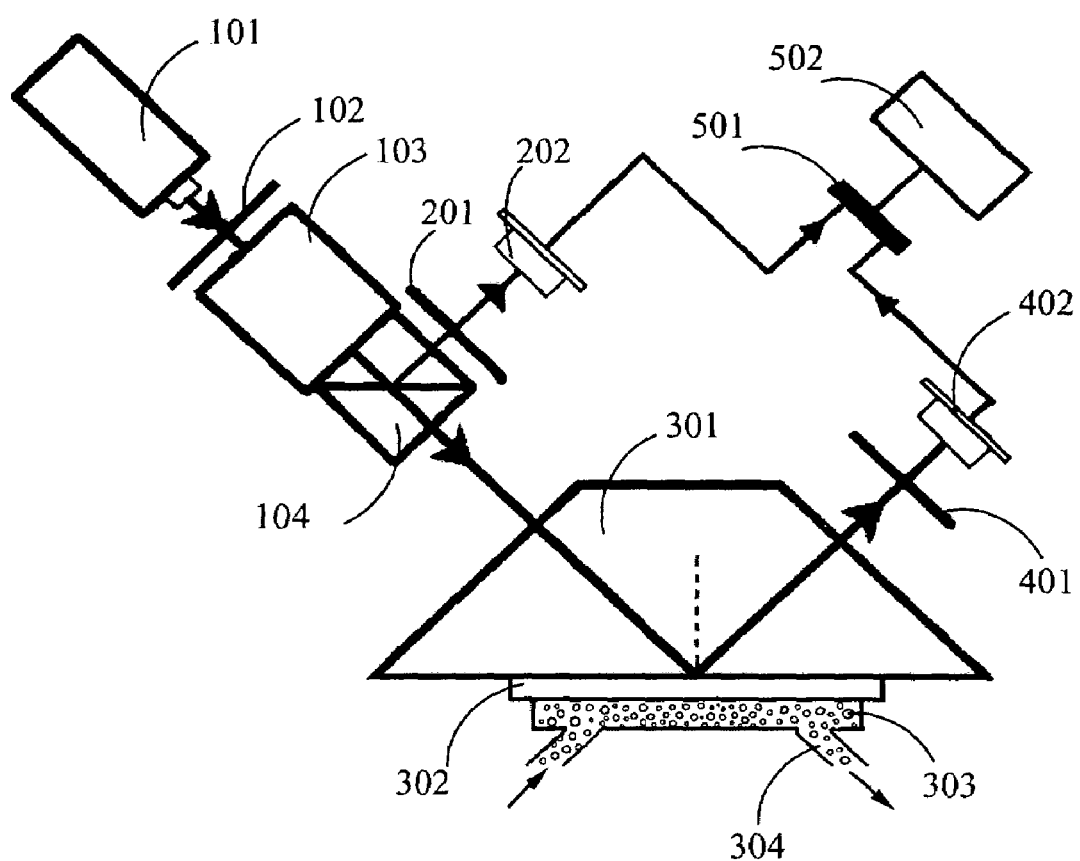
FIG. 8 is a schematic view of a SPR sensor according to the present invention.

The sensing unit 300 is used for receiving another portion, about 96%, of the beam of light to induce a phase retardation change between the p- and s-polarization components due to SPR associated with a sample. It is understood by those skilled in the art that any SPR coupling schemes, such as prism coupling, waveguide coupling, and grating coupling, may be applied to the present invention. In the embodiment, a prism coupling scheme (prism/metal layer/sample) is preferably used and the configuration thereof is shown in FIGS. 7 and 8. In this configuration, the prism coupling scheme comprises a prism 301, a transducing layer 302 coated on a surface of the prism to serve as a sensing surface, and a sample flow chamber 304 associated with the prism 301 for allowing a sample 303 flowing through the sensing surface. The prism 301 can be made by transparent dielectric material such as plastic or glass in order to enhance the momentum of light to match with the momentum of SPW. In this embodiment, a dove prism made by BK7 glass is employed. The transducing layer 302 is commonly made by conducting material such as gold or silver. In this embodiment, a gold thin layer, about 48 nm, is employed because of its good chemical resistance. The thickness of such a layer is normally at the range of 20 nm to 80 nm depending on applications and material selection. The sample 303 is normally used in aqueous form. Glycerin and water mixtures in the concentration of weight percentage from 0% to 16% were used in this embodiment. The sample flow chamber 304 is designed for permitting the sample 303 flowing in and out the chamber 304 while contacting the sensing surface. Since only the p-polarization component is affected by the SPR effect, and the s-polarization component is kept intact, a phase retardation change between the p- and s-polarization components can be introduced by the SPR according to the concentration of weight percentage of the sample.

As shown in FIG. 8, the probe unit 400 is used to provide a probe signal indicating the phase retardation change by receiving the light after SPR. Similar to the reference unit 200, the probe unit 400 comprises a polarizer 401 and a photodetector 402. The polarizer 401 is oriented so that the p- and s-polarized components can interfere with each another. Then the photodetector 402 is used to capture the optical intensity variation. Depending on the designed applications, the photodetector 402 can be a photo-diode or a photo charge coupled device (CCD). In the embodiment, a silicon photodiode is employed as the photodetector 402.

As shown in FIG. 8, the detection unit 500, which is connected between the reference unit 200 and the probe unit 400, comprises a phase meter 501 and a microprocessor 502. The phase meter 501 is employed to measure a differential phase between the reference signal and the probe signal so that the microprocessor 502 is able to determine biological, biochemical, or chemical characteristics of the sample in accordance with the differential phase.

Figure 9:
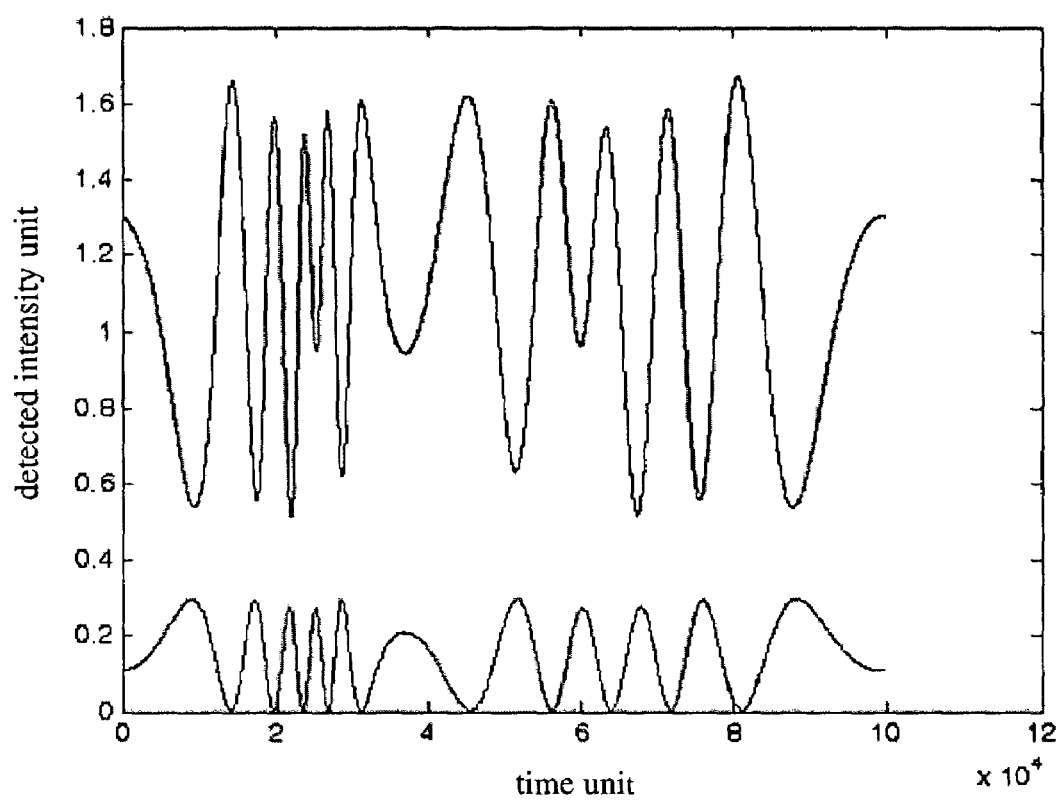
FIG. 9 shows typical collected waveforms from the probe and reference units.
Figure 10:
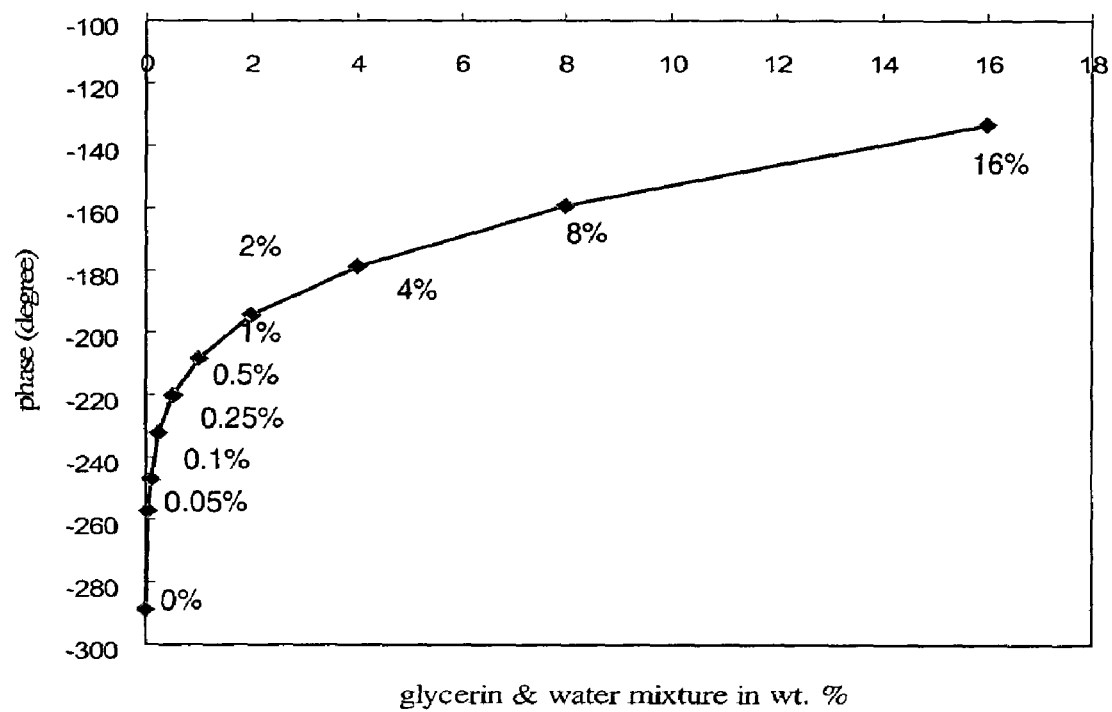
FIG. 10 shows SPR phase measurement obtained from glycerin and water mixtures of various concentrations: 0%, 0.05%, 0.1%, 0.25%, 0.5%, 1%, 2%, 4%, 8% and 16% in weight percentage.
Figure 11:
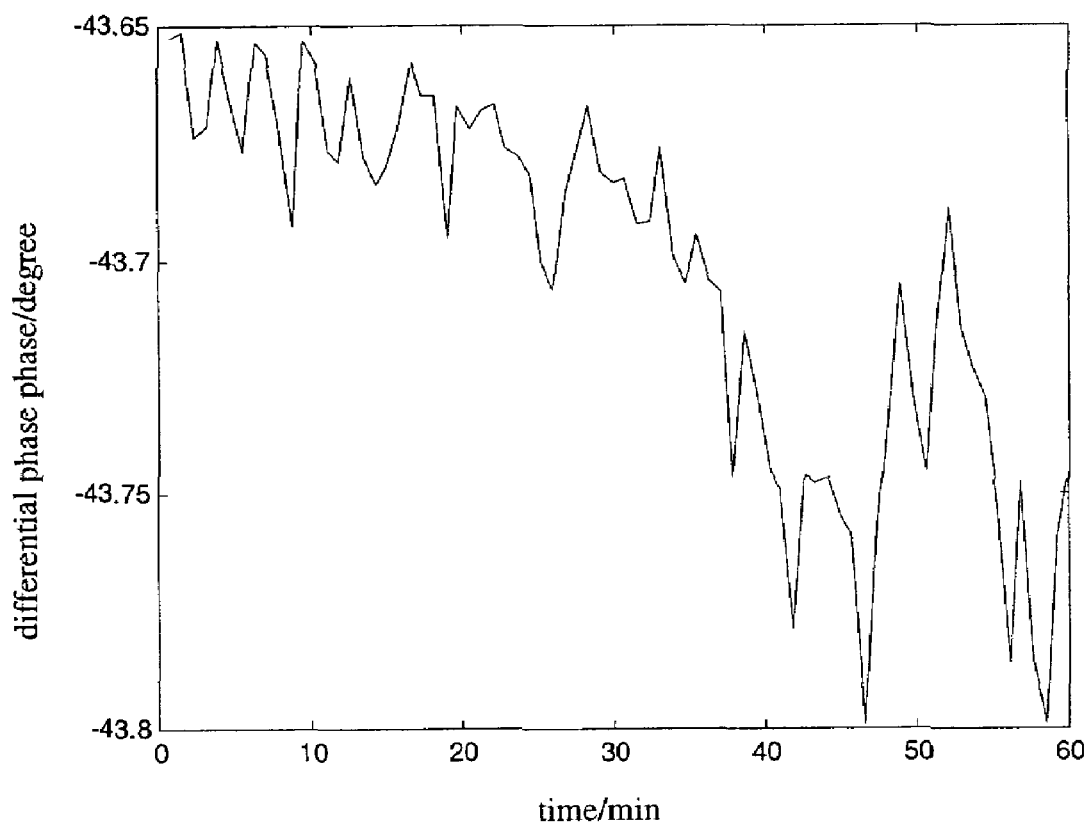
FIG. 11 is a graph showing system stability measured over an hour.

Typical signal waveform collected from the probe unit and reference unit are shown in FIG. 9. After processed by the phase extraction analysis program, the differential phase value between the probe and reference signals is obtained from the signal waveforms. To demonstrate the performance of the present invention, the concentration measurement of glycerin and water mixtures from 0% to 16% in weight percentage with the corresponding refractive index unit (RIU) ranging from 1.3330 to 1.3521 was conducted. The experimental differential phase variation versus glycerin concentration is shown in FIG. 10. According to this plot, the phase response was found to be $1.7 \times 10^{-6}$ RIU/degree in the most sensitivity region and the system stability was also measured to be less than 0.15° within an hour as shown in FIG. 11. Using this stability value as the phase resolution, the calculated system sensitivity was therefore $2.6 \times 10^{-7}$ RIU.

The SPR sensor according to the present invention generates a required signal in the time domain through modulating a phase retardance of a beam using a LCM, hence leading to much reduced system hardware complexity. More importantly, the removal of angular measurement also enables full field imaging of the SPR sensor surface, which is a prerequisite for two-dimensional sensor arrays. In addition, signal to noise ratios may be easily enhanced according to needs through signal averaging. Digital data processing such as narrowband filtering may also be applied to the invention to improve the measurement precision.

While we have hereinbefore described embodiments of this invention, it is understood that our basic constructions can be altered to provide other embodiments which utilize the processes and compositions of this invention. Consequently, it will be appreciated that the scope of this invention is to be defined by the claims appended hereto rather than by the specific embodiments which have been presented hereinbefore by way of examples.

The invention claimed is:

1. An optical sensing device comprising:
   a source unit, comprising:
      a source emitting a beam of light containing p-polarization and s-polarization components, and
      a phase modulator modulating a phase retardation between the p-polarization and s-polarization components;
   a reference unit, configured to receive a first part of the light, thereby providing a reference signal indicating the modulated phase retardation;
   a SPR sensing unit, configured to receive a second part of the light, thereby inducing a phase retardation change between the p-polarization and s-polarization components due to SPR associated with a sample;
   a probe unit, configured to receive the light passing the SPR sensing unit thereby providing a probe signal indicating the phase retardation change induced by the SPR sensing unit; and
   a detection unit, coupled between the reference unit and the probe unit to detect biological, biochemical, or chemical characteristics of the sample by comparing the reference signal with the probe signal.

2. The optical sensing device according to claim 1, wherein the phase modulator is a liquid crystal modulator and the phase retardation is continuously modulated by the liquid crystal modulator.

3. The optical sensing device according to claim 2, wherein the liquid crystal modulator comprises one liquid crystal layer.

4. The optical sensing device according to claim 2, wherein the liquid crystal modulator comprises two or more liquid crystal layers stacked together.

5. The optical sensing device according to claim 2, wherein the liquid crystal modulator comprises two mirrors and a liquid crystal layer disposed between the mirrors.

6. The optical sensing device according to claim 1, wherein the source of the source unit is a gas laser, a solid state laser, a laser diode, a light emitting diode, or a broad band white light source.

7. The optical sensing device according to claim 1, wherein the source unit further comprises:
a polarizer for selecting an intensity ratio between the p-polarization and s-polarization components of the light emitted from the source; and
a beam splitter for separating the modulated light into the first part and the second part.

8. The optical sensing device according to claim 1, wherein the reference unit comprises:
a polarizer employed to form an interference between the p-polarization and s-polarization components of the first part of light; and
a photodetector detecting the interference and converting an optical intensity variation of the interference to the reference signal indicating the phase retardation.

9. The optical sensing device according to claim 8, wherein the photodetector is a photo-diode or a photo charge coupled device.

10. The optical sensing device according to claim 1, wherein the sensing unit comprises:
a prism;
a transducing layer coated on a surface of the prism to serve as a sensing surface; and
a sample flow chamber associated with the prism allowing the sample flowing through the sensing surface.

11. The optical sensing device according to claim 1, wherein the probe unit comprises:
a polarizer employed to form an interference between the p-polarization and s-polarization components of the second part of light; and
a photodetector detecting the interference and converting an optical intensity variation of the interference to the probe signal indicating the phase retardation change induced by the SPR sensing unit.

12. The optical sensing device according to claim 11, wherein the photodetector is a photo-diode or a photo charge coupled device.

13. The optical sensing device according to claim 1, wherein the detection unit comprises:
a phase meter for measuring a differential phase between the reference signal and the probe signal; and
a microprocessor for determining the biological, biochemical, or chemical characteristics of the sample in accordance with the differential phase.

14. A method of detecting biological, biochemical, or chemical characteristics of a sample comprising:
transmitting a beam of light containing p-polarization and s-polarization components;
modulating a phase retardation between the p-polarization and s-polarization components;
providing a reference signal indicating the phase retardation by receiving a first part of the light;
receiving a second part of the light to induce a phase retardation change between the p-polarization and s-polarization components due to SPR associated with a sample;
providing a probe signal indicating the phase retardation change by receiving the light after SPR associated with the sample; and
detecting biological, biochemical, or chemical characteristics of the sample by comparing the probe signal with the reference signal.

15. The method according to claim 14, wherein the phase retardation is continuously modulated by a liquid crystal modulator through varying a drive voltage of the liquid crystal modulator.

16. The method according to claim 15, wherein the drive voltage of the liquid crystal modulator is varied from 0v to 13v and a frequency of the liquid modulator is set to be 10 Hz.

17. The method according to claim 15, wherein the liquid crystal modulator comprises one liquid crystal layer, and a thickness of the liquid crystal layer is designed so that a modulation depth of the liquid crystal modulator is greater than $2\pi$.

18. The method according to claim 15, wherein the liquid crystal modulator comprises two or more liquid crystal layers stacked together to form a multi-layered modulator, and the number of the liquid crystal layers and a thickness of each liquid crystal layer are designed so that a modulation depth of the liquid crystal modulator is greater than $2\pi$.

19. The method according to claim 15, wherein the liquid crystal modulator comprises two mirrors and a liquid crystal layer disposed between the mirrors, and a thickness of the liquid crystal layer and a position of the mirrors and liquid crystal layer are designed so that a modulation depth of the liquid crystal modulator is greater than $2\pi$.

20. The method according to claim 14, wherein said transmitting a beam of light further comprises selecting an intensity ratio between the p-polarization and s-polarization components.

21. The method according to claim 14, wherein said providing a reference signal comprises:
generating an interference between the p-polarization and s-polarization components of the first part of light by means of a polarizer; and
converting an optical intensity variation of the interference to the reference signal.

22. The method according to claim 21, wherein the reference signal is used to monitor an effect of temperature variation.

23. The method according to claim 14, wherein said receiving a second part of light to induce a phase retardation change comprises:
allowing the sample flowing through a chamber of an SPR sensor; and
subjecting the second part of the light to passing through the SPR sensor so that the phase retardation between the p-polarization and s-polarization components of the second part of light is changed due to the SPR at the SPR sensor.

24. The method according to claim 14, wherein said providing a probe signal comprises:
generating an interference between the p-polarization and s-polarization components of the light after SPR by means of a polarizer; and
converting an optical intensity variation of the interference to the probe signal.

25. The method according to claim 14, wherein said detecting the biological, biochemical, or chemical characteristics of the sample comprises:
measuring a differential phase between the reference signal and the probe signal; and
determining biological, biochemical, or chemical characteristics of the sample in accordance with the differential phase.

* * * * *